United States Patent [19]

Shimada et al.

[11] Patent Number: 4,819,751

[45] Date of Patent: Apr. 11, 1989

[54] VALVULOPLASTY CATHETER AND METHOD

[75] Inventors: Lynn M. Shimada, Fullerton; Guy R. Lowery, Mission Viejo; Glen L. Lieber, Yorba Linda, all of Calif.

[73] Assignee: Baxter Travenol Laboratories, Inc., Deerfield, Ill.

[21] Appl. No.: 109,761

[22] Filed: Oct. 16, 1987

[51] Int. Cl.⁴ .......................................... A61M 29/02
[52] U.S. Cl. ..................................... 128/344; 604/104
[58] Field of Search ...................... 604/104, 96-103; 128/1 D, 344, 325

[56] References Cited

U.S. PATENT DOCUMENTS

| | | |
|---|---|---|
| 4,439,186 | 3/1984 | Kuhl . |
| 4,448,195 | 5/1984 | LeVeen et al. . |
| 4,527,549 | 7/1985 | Gabbay . |
| 4,546,759 | 10/1985 | Solar . |
| 4,614,188 | 9/1986 | Bazell et al. . |
| 4,619,261 | 10/1986 | Guerriero . |
| 4,637,396 | 1/1987 | Cook . |
| 4,646,719 | 3/1987 | Neuman et al. ............... 128/344 X |
| 4,664,125 | 5/1987 | Pinto . |
| 4,665,925 | 5/1987 | Miller . |
| 4,692,148 | 9/1987 | Kantrowitz et al. . |

FOREIGN PATENT DOCUMENTS 1566674  2/1978  United Kingdom .

Primary Examiner—Stephen C. Pellegrino
Attorney, Agent, or Firm—Gordon L. Peterson

[57] ABSTRACT

A valvuloplasty catheter comprising a catheter body having a through lumen, a tube extending through the lumen and having a distal end portion extending distally beyond the distal end of the catheter body and movable axially in the lumen relative to the catheter body. A radially expandable and axially contractable balloon is coupled, respectively, to the catheter body at the distal end portion of the tube. The balloon has a central region between the opposite end portions of the balloon which is of greater radial dimension in the relaxed condition than the opposite end portions and transition regions between the central region and the opposite end portions. The catheter body has a distal end portion which is less stiff than the region of the catheter body immediately proximal of the distal end portion of the catheter body.

10 Claims, 2 Drawing Sheets

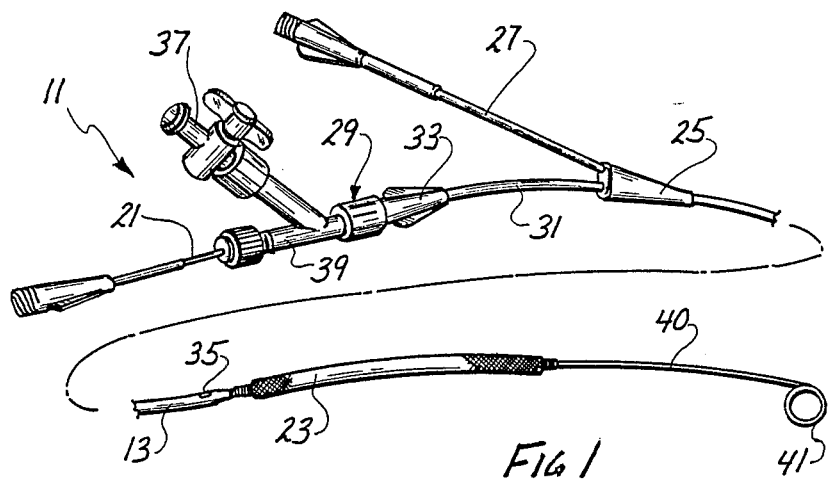
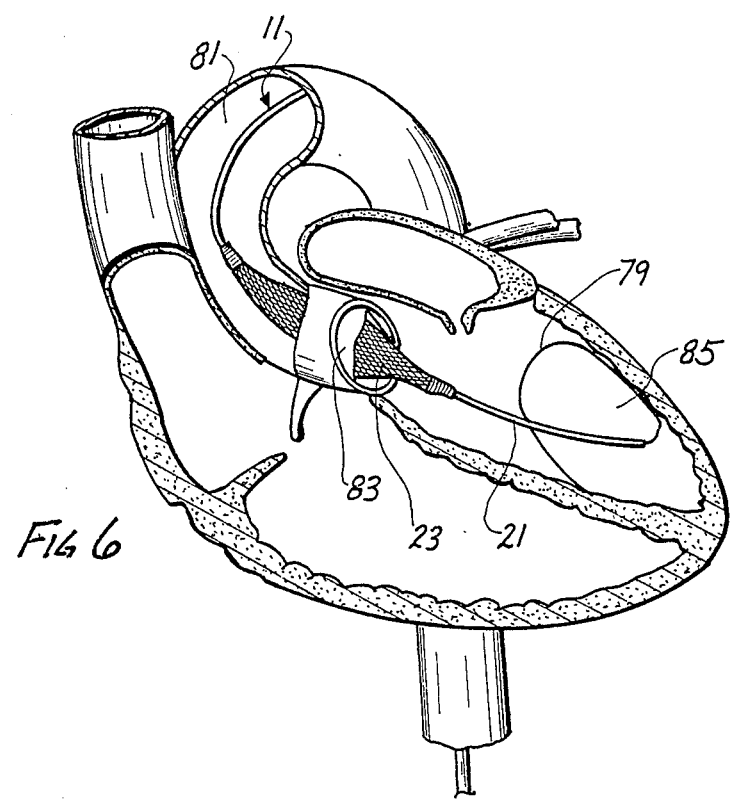

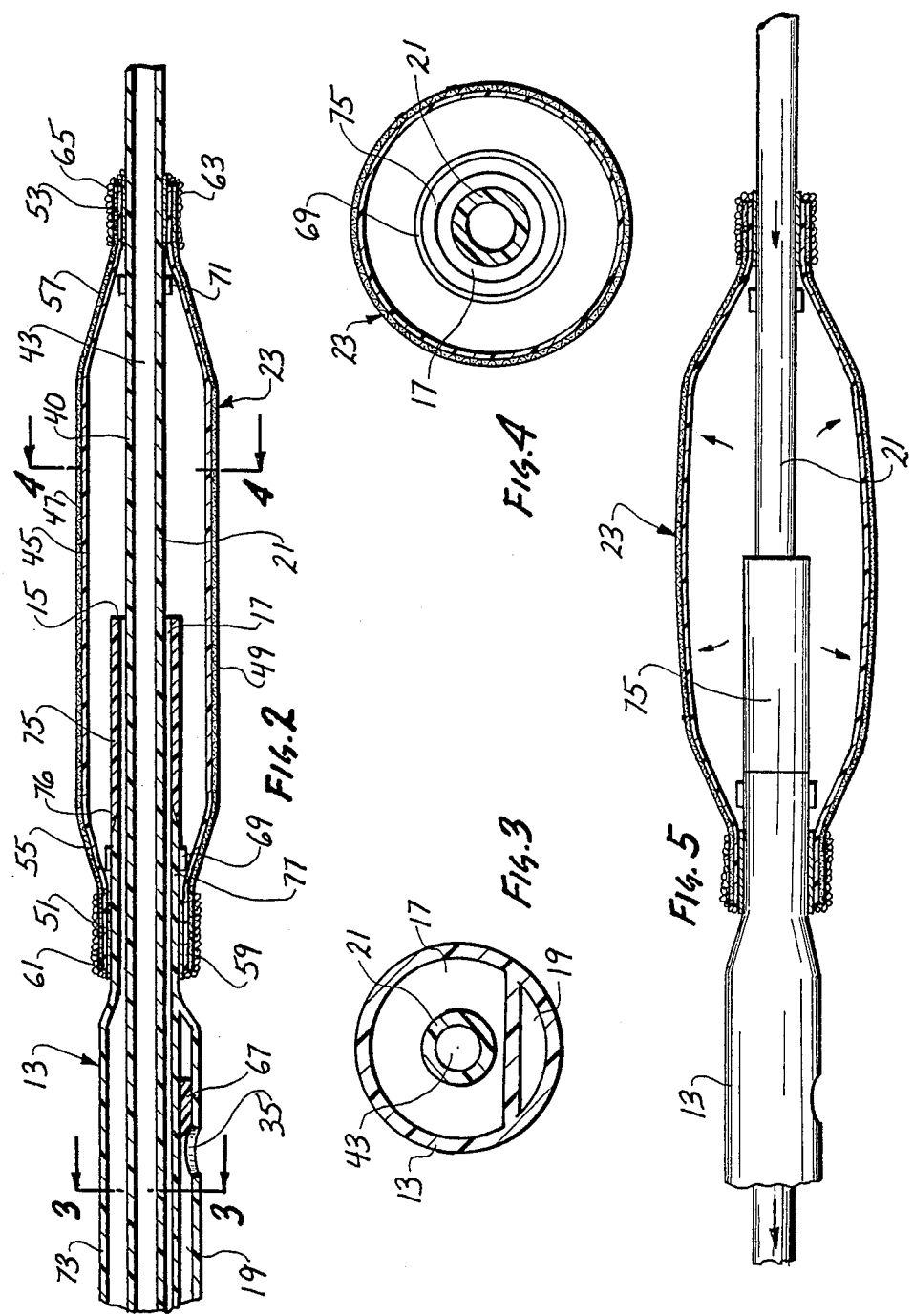

VALVULOPLASTY CATHETER AND METHOD

BACKGROUND OF THE INVENTION

A procedure known as balloon valvuloplasty is used to treat calcified, stenotic heart valves. In this procedure, a catheter having a deflated balloon is inserted through a vein or artery into the heart until the balloon is within the heart valve to be treated. The balloon is then inflated to dilate the diseased valve. After dilation, the balloon is deflated and withdrawn from the cardiovascular system of the patient.

Currently, this procedure is performed with large diameter, conventional polyethylene balloon dilator catheters. In order to be large enough to dilate a heart valve, the balloon must have a relatively large diameter when inflated. On the other hand, in order to be able to advance the catheter and balloon through a vessel of the patient to the heart, it must present a small diameter profile when deflated. To accommodate both of these requirements, the conventional dilator catheter has a balloon of large diameter which is prefolded prior to insertion into the vessel to make the cross section smaller so that the balloon can be advanced through the vessel to the heart.

Carrying out of the balloon valvuloplasty procedure with this kind of dilator catheter creates a number of problems. For example, the folds in the balloon form, in effect, radially extending wings or webs which tend to cause trauma and bleeding during withdrawal of the catheter. In addition, the large diameter folded balloon occupies an undesirably large portion of the cross-sectional area of the vessel during insertion and withdrawal of the catheter.

The radial dimensions of the balloon must increase substantially when inflated in order that the balloon can be small enough to pass through a vessel leading to the heart and be large enough in the inflated condition to dilate a heart valve. For this reason, it is not possible to safely use a conventional distensible latex balloon because of the likelihood that the elastic limit of the balloon would be exceeded.

One kind of nephrostomy catheter and a catheter for dilating blood vessels use a balloon which is radially expandable and axially contractable. However, these balloons are not able to radially expand to the relatively large diameter necessary to dilate a heart valve, and they have an abrupt change of stiffness within the balloon which would be undesirable for treating heart valves.

SUMMARY OF THE INVENTION

This invention provides a valvuloplasty catheter and method which overcome the disadvantages noted above. This invention eliminates the abrupt change of stiffness within the balloon and the use of a balloon having folds in its outer periphery. This invention reduces the tendency for trauma and bleeding during withdrawal of the catheter and tends to reduce the size of the portion of the cross-sectional area of the vessel which is blocked by the balloon.

To avoid an abrupt change of stiffness of the catheter within the balloon, the catheter includes a catheter body having a distal end portion which is less stiff than the region of the catheter body proximally of the distal end portion. The distal end portion of the catheter body is at least partially within the balloon. In a preferred construction, the catheter body includes a main body, and the distal end portion is joined to the main body of the catheter body.

With this invention, the radially expandable and axially contractable balloon is made capable of undergoing substantial radial expansion by providing the balloon with a central region between the opposite end portions of the balloon, with the central portion being of greater radial dimension in the relaxed condition than the opposite end portions and by providing first and second transition regions of the balloon between the central region and the opposite end portions, respectively. The transition regions blend the narrower end portions with the wider central region and are preferably tapered with a frusto-conical configuration being considered optimum. The central region is preferably cylindrical in the relaxed condition and is of small enough diameter in the relaxed condition to pass through a vein or artery to the heart.

The use of a reinforced balloon guards against rupture of the balloon when inflated and consequent injury to the patient. To this end, the balloon advantageously includes a distensible bladder and a reinforcing sheath receiving the bladder.

In a preferred construction, a catheter body has a distal end and a through lumen, and the catheter includes a tube extending through the through lumen and movable axially in the through lumen relative to the catheter body and having a distal end portion extending distally beyond the distal end of the catheter body. The opposite end portions of the balloon are coupled, respectively, to the catheter body and the distal end portion of the tube. The balloon is inflatable through the catheter body, and this may be accomplished, for example, by the through lumen or by a separate balloon inflation lumen.

A heart valve can be dilated by advancing a reinforced, radially expandable and axially contractable balloon with a central section having a longitudinally unfolded outer perimeter when the balloon is deflated through a vessel of the patient into the heart to place the balloon within a valve of the heart. The balloon is then inflated to radially expand and axially contract the balloon to dilate the valve. The balloon is then deflated and reinflated as necessary to accomplish the necessary heart dilation function. Following this, the catheter is withdrawn from the cardiovascular system of the patient.

The invention, together with additional features and advantages thereof, may best be understood by reference to the following description taken in connection with the accompanying illustrative drawing.

BRIEF DESCRIPTION OF THE DRAWING

FIG. 1 is a perspective view of a catheter constructed in accordance with the teachings of this invention.

FIG. 2 is an enlarged, fragmentary sectional view taken through the region of the catheter at the balloon, with the balloon deflated.

FIGS. 3 and 4 are enlarged sectional views taken generally along lines 3—3 and 4—4, respectively, of FIG. 2.

FIG. 5 is a view similar to FIG. 2 with the balloon being inflated.

FIG. 6 is a view partially in section of a human heart showing the catheter being used to dilate a heart valve.

DESCRIPTION OF THE PREFERRED EMBODIMENT

FIG. 1 shows a catheter 11 which comprises a catheter body 13 having a distal end 15 (FIG. 2), a through lumen 17 (FIGS. 2 and 3), and an infusion lumen 19, a tube 21 extending through the through lumen 17, and a radially expandable and axially contractable balloon 23. The catheter body 13 extends proximally through a fitting 25, which couples a tube 27 to the infusion lumen 19 in a conventional manner, to a Y-fitting 29 via a proximal portion 31 of the catheter body and a hub 33. With this arrangement, a liquid can be infused through the tube 27, the infusion lumen 19 and an infusion port 35 (FIG. 2) to the vascular system of the patient. Also, the balloon 23 can be inflated and deflated through a leg 37 of the Y-fitting 29 and the through lumen 17.

The tube 21 extends through a leg 39 of the Y-fitting 29, the tube 31, the through lumen 17, the balloon 23 and distally of the balloon. In this embodiment, the tube 21 has a distal portion 40 extending distally beyond the distal end of the catheter body 13 and a distal pigtail tip portion 41. The tube 21 is movable axially in the through lumen 17 relative to the catheter body 13 and has an axial passage 43 (FIG. 2) extending completely through it. The balloon 23 is reinforced, and in this embodiment, it comprises a distensible bladder 45 of urethane or other suitable distensible material and a reinforcing sheath 47 (FIG. 2) tightly receiving the bladder. Although various constructions are possible, in this embodiment, the sheath 47 is a woven braid, the pore structure of which is sealed with a suitable distensible material, such as urethane. The sheath 47 prevents the bladder 45 from extruding into the crevices that might be presented by the heart valve and axially contracts as it is radially expanded. Preferably, the sheath is formed from braided dacron fibers.

The balloon 23 has a central region 49 which has an outer periphery which is devoid of longitudinal folds. In fact, the outer periphery of the central region 49 is entirely unfolded in both the deflated or relaxed condition shown in FIG. 2 and the inflated condition.

The balloon 23 also has opposite end portions 51 and 53 which are coupled, respectively, to the catheter body 13 and the tube 21. The central region 49 lies between the opposite end portions 51 and 53 and is of greater radial dimension in the relaxed condition than the opposite end portions. Transition regions 55 and 57 lie between the central region 49 and the opposite end portions 51 and 53, respectively. At least one, and preferably both of the transition regions 55 and 57 are tapered. In a preferred construction, the end portions 51 and 53 and the central region 49 are cylindrical, with the central region having the greater diameter, and both of the transition regions 55 and 57 are frusto-conical in the relaxed condition. Although the transition regions 55 and 57 need not be tapered, this is preferred because it minimizes the likelihood of undesirable stress concentrations in the balloon.

The end portions 51 and 53 are attached to the catheter body 13 and the tube 21, respectively, using conventional techniques. For example, the end portion 51 is attached by providing a rigid metal bushing 59 on the catheter body 13 and tightly retaining the end portion 51 against the bushing with a filament 61 wound on the end portion 51. The end portion 53 is similarly attached to the tube 21 using a bushing 63 and filament 65.

A plug 67 (FIG. 2) closes off the infusion lumen 19 on the distal side of the port 35. Radiopaque markers 69 and 71 are suitably affixed to the catheter body 13 and the tube 21 within the balloon 23.

The catheter body 13 includes a main body 73 which extends from the proximal end of the catheter body to a location 76 just within the balloon and a distal end portion 75 joined to the main body 73 and lying entirely within the balloon. The distal end portion 75 is less stiff than the main body 73. A distal region 77 of the main body 73 is of reduced diameter, and in this embodiment, the distal region 77 is the only portion of the main body 73 lying within the balloon 23. The distal end region 77 extends all the way to the distal end portion 75 where the two are joined in end-to-end relationship in a conventional manner, such as by bonding the two together with heat and pressure. The distal end portion 75, in this embodiment, is cylindrical and extends from a location radially inwardly of the transition region 55 all the way to the distal end 15. The distal end 15 lies within the balloon 23 so that the through lumen 17 can serve, not only as a passageway for the tube 21, but also as a balloon inflation lumen for the balloon 23.

In using the catheter 11 to dilate a heart valve, the catheter is advanced over a prepositioned guidewire 79 (FIG. 6) into the heart. By way of example, the catheter 11 may be advanced through the aorta 81 to the aortic valve 83, with the distal end of the balloon 23 and a distal length of the tube 21 extending into the left ventricle 85.

With the balloon 23 properly positioned in the aortic valve 83, the balloon 23 is inflated with a suitable inflation media as shown in FIG. 5 to radially expand and axially contract the balloon. The axial contraction of the balloon 23 moves the tube 21 proximally in the lumen 17 to allow the radial expansion of the balloon to continue. The radial expansion of the balloon 23 dilates the aortic valve 83. The balloon is then deflated, and the process of inflating and deflating the balloon to repeatedly dilate the aortic valve 83 may be carried out as many times as desired by the physician. When the heart valve has been dilated to the satisfaction of the physician, the catheter is withdrawn from the heart and cardiovascular system of the patient. Of course, this same procedure may be repeated for other heart valves.

During the insertion and withdrawal of the catheter 11, the balloon 23 is deflated, and as such, is only of slightly larger diameter than the diameter of the main body 73 of the catheter body 13. As such, the deflated balloon can pass through the vessel, i.e., vein or artery, of the patient to the heart. However, because of the presence of the tapered transition regions 55 and 57, the balloon 23 can be inflated to a much larger diameter which is suitable for dilating the relatively large heart valves. The tapering of the transition regions 55 and 57 facilitates movement of the catheter 11 through the cardiovascular system with these transition regions providing a minimum of obstruction.

Although an exemplary embodiment of the invention has been shown and described, many changes, modifications and substitutions may be made by one having ordinary skill in the art without necessarily departing from the spirit and scope of this invention.

I claim:

1. In a catheter which includes a catheter body having a distal end and a through lumen, a tube extending through the through lumen and movable axially in the through lumen relative to the catheter body and having a distal end portion extending distally beyond the distal end of the catheter body, and a radially expandable and axially contractable balloon having opposite end portions coupled, respectively, to the catheter body and the distal end portion of the tube and inflatable through the catheter body whereby inflation of the balloon from a relaxed uninflated condition expands the balloon radially and contracts the balloon axially, the improvement comprising:

said catheter body having a distal end portion at least partially within the balloon which is less stiff than the region of the catheter body proximally of the distal end portion of the catheter body to avoid an abrupt change of stiffness within the balloon, said catheter body including a main body and said distal end portion of said catheter body being a separate member and being joined to the main body of the body.

2. An improvement as defined in claim 1 wherein said distal end portion of said catheter body is entirely within said balloon.

3. An improvement as defined in claim 1 wherein said balloon has a central region between said opposite end portions of the balloon of greater radial dimension in the relaxed condition than said opposite end portions and first and second transition regions between the central region and the opposite end portions, respectively, and the central region has an outer periphery which is devoid of longitudinal folds.

4. An improvement as defined in claim 3 wherein at least one of the transition regions is tapered.

5. An improvement as defined in claim 3 wherein each of the transition regions is generally of frusto-conical configuration.

6. An improvement as defined in claim 3 wherein said central region is generally cylindrical in the relaxed condition.

7. An improvement as defined in claim 3 wherein said balloon includes a distensible bladder and a reinforcing sheath receiving said bladder, said bladder when in a relaxed state having a central region of greater radial dimension than end portions of the bladder.

8. A method of dilating a heart valve comprising:
providing a catheter having a reinforced, radially expandable and axially contractable, inflatable balloon with a central region with a longitudinally unfolded outer periphery when the balloon is deflated;
advancing the catheter with the balloon deflated through a vessel of a patient into the heart of the patient to place the balloon within a valve of the heart;
inflating the balloon to radially expand and axially contract the balloon to dilate the valve;
deflating the balloon; and
withdrawing the catheter from the cardiovascular system of the patient.

9. A method as defined in claim 8 including alternately carrying out said steps of inflating and deflating prior to said step of withdrawing.

10. A method as defined in claim 8 wherein the step of providing includes providing a catheter body having a distal end portion which is less stiff than the region of the catheter body proximally of the distal end portion of the catheter body and said distal end portion of the catheter body being at least partially within the balloon.

* * * * *

UNITED STATES PATENT AND TRADEMARK OFFICE
CERTIFICATE OF CORRECTION

PATENT NO. : 4,819,751

DATED : Apr. 11, 1989

INVENTOR(S) : Lynn M. Shimada et al

It is certified that error appears in the above-identified patent and that said Letters Patent is hereby corrected as shown below:

```
Column 5, the last line of claim 1 before "body"
insert -- catheter --.
```

Signed and Sealed this

Twenty-third Day of January, 1990

Attest:

JEFFREY M. SAMUELS

Attesting Officer — Acting Commissioner of Patents and Trademarks